United States Patent [19]

Shultz et al.

[11] 4,158,055

[45] Jun. 12, 1979

[54] ADMINISTRATION OF 16α,17α-CYCLOPENTYLIDENEDIOXY-9α-FLUORO-11β,21-DIHYDROXY-1,4-PREGNA-DIENE-3,20-DIONE 21-ACETATE

[75] Inventors: Walter Shultz, Spring Valley, N.Y.; George M. Sieger, Montvale; Charles Krieger, Clifton, both of N.J.

[73] Assignee: American Cyanamid Company, Stamford, Conn.

[21] Appl. No.: 754,917

[22] Filed: Dec. 28, 1976

Related U.S. Application Data

[63] Continuation-in-part of Ser. No. 584,678, Jun. 6, 1975, abandoned, which is a continuation-in-part of Ser. No. 389,302, Aug. 17, 1973, abandoned.

[51] Int. Cl.² .............................................. A61K 31/58
[52] U.S. Cl. ............................. 424/241; 260/239.55 D
[58] Field of Search ............... 260/239.55 D; 424/241

[56] References Cited

U.S. PATENT DOCUMENTS

| | | | |
|---|---|---|---|
| 3,048,581 | 8/1962 | Fried | 260/239.55 D |
| 3,053,836 | 9/1962 | Fried | 260/239.55 D |
| 3,541,602 | 11/1970 | Diassi | 260/239.55 D |
| 3,856,954 | 12/1974 | Jackson | 424/241 |
| 3,867,528 | 2/1975 | Ritter et al. | 424/241 |

FOREIGN PATENT DOCUMENTS

| | | | |
|---|---|---|---|
| 894810 | 4/1962 | United Kingdom | 260/239.55 D |
| 928150 | 6/1963 | United Kingdom | 424/240 |

OTHER PUBLICATIONS

Applezweig, Steroid Drugs, p. 307, McGraw-Hill Book Co., Inc. 1962.

McKenzie, "Percutaneous Absorption of Steroids", vol. 86 (1962), Archives of Dermatology, pp. 611–614.

McKenzie, "Topical Activites of Betamethusone Esters in Man", Archives of Dermatology, vol. 89, (1964), pp. 741–746.

*Primary Examiner*—Ethel G. Love
*Attorney, Agent, or Firm*—Claude J. Caroli

[57] ABSTRACT

A method of treating topical inflammation in mammals by the administration of 16α,17α-cyclopentylidene-dioxy-9α-fluoro-11β,21-dihydroxy-1,4-pregnadiene-3,20-dione 21-acetate in a pharmaceutically acceptable carrier.

7 Claims, No Drawings

ADMINISTRATION OF 16α,17α-CYCLOPENTYLIDENEDIOXY-9α-FLUORO-11β,21-DIHYDROXY-1,4-PREGNADIENE-3,20-DIONE 21-ACETATE

This application is a continuation-in-part of our pending application Ser. No. 584,678, filed June 6, 1975, now abandoned, which, in turn, is a continuation-in-part of our application Ser. No. 389,302 filed Aug. 17, 1973, and now abandoned.

DESCRIPTION OF THE INVENTION

It is well known that steroids can be used topically to relieve inflammation and their use in this manner has met with varying degrees of success. The need has existed for more potent topically useful steroids. We have now found that 16α17α-cyclopentylidenedioxy-9α-fluoro-11β,21-dihydroxy-1,4-pregnadiene-3,20-dione 21-acetate as the active component in topical compositions is a highly effective anti-inflammatory agent. This compound is more effective than structurally similar steroids used in the past as topically anti-inflammatory agents as indicated by the vasoconstriction assay.

The active component of the present compositions, 16α17α-cyclopentylidenedioxy-9α-fluoro-11β,21-dihydroxy-1,4-pregnadiene-3,20-dione 21-acetate is prepared by treating a suspension of 9α-fluoro-11β,16α,17,21-tetrahydroxy-1,4-pregnadiene-3,20-dione (triamcinolone, a commercially available product) with perchloric acid and cyclopentanone. The suspension is stirred until solution is complete and then stored in a cold room. The product 16α,17α-cyclopentylidenedioxy-9α-fluoro-11β,21-dihydroxy-1,4-pregnadiene-3,20-dione is collected, washed with n-hexane and air dried.

The above product is treated with acetic anhydride in pyridine, stirred for about 2½ hours and then poured onto a mixture of ice and water. The steroid acetate is collected by filtration and air dried.

In order to demonstrate the superiority of the cyclopentylidene derivative, Applicants prepared the adjacent homologs, i.e., the cyclobutylidene and cyclohexylidene derivatives and submitted them for a comparative vasoconstriction assay. This assay is described in the following publications: (1) "Bioassay System for Formulations of Topically Applied Glucocorticosteroids", R. B. Stoughton, Archives of Dermatology, 106 825–827 (1972). (2) "Topical Activities of Betamethasone Esters in Man", A. W. McKenzie and R. M. Atkinson, Archives of Dermatology, 89, 741–746 (1964). (3) "Method For Comparing Percutaneous Absorption of Steroids", A. W. McKenzie and R. B. Stoughton, Archives of Dermatology, 86 608–610 (1962). (4) "Percutaneous Absorption of Steroids", A. W. McKenzie, Archives of Dermatology 86, 611–614 (1962).

The compounds were prepared for testing by dissolving each in 95% ethanol to the desired concentration w/v. About 0.01 cc of each solution was applied to the volar surface of the forearm of volunteers ranging from 18–60 years of age. Eight to ten sites were applied to the two forearms. Each site was about 2.5 cm in diameter. The sites were protected by a perforated plastic guard which was secured at the ends with tape. The guards remained in place for 16 hours, then removed. The forearms were immediately washed with soap and water. Two hours later the forearms were inspected by an experienced reader who did not know what had been applied or where. The readings determined the presence and intensity (blanching) at each site. The scoring is as follows: 0=no vasoconstriction; 1=just discernable vasoconstriction; 2=moderate vasoconstriction; and 3=marked vasoconstriction.

Two separate evaluations were conducted. The first involved 30 volunteers and compared the vasoconstrictive properties of triamcinolone acetonide, 16α,17α-cyclopentylidenedioxy-9α-fluoro-11β,21-dihydroxy-1,4-pregnadiene-3,20-dione 21-acetate and the homologous cyclohexylidene derivative thereof. Point totals indicating the degree of vasoconstriction elicited appear in Table I.

TABLE I

| Compound | Concentration | Total Points |
|---|---|---|
| 16α,17α-Cyclopentylidenedioxy-9α-fluoro-11β,21-dihydroxy-1,4-pregnadiene-3,20-dione 21-acetate | 0.05% | 39 |
|  | 0.10% | 52 |
| 16α,17α-Cyclohexylidenedioxy-9α-fluoro-11β,21-dihydroxy-1,4-pregnadiene-3,20-dione 21-acetate | 0.05% | 14 |
|  | 0.10% | 20 |
| 9α-Fluoro-11β,21-dihydroxy-16α,17α-isopropylidenedioxy-1,4-pregnadiene-3,20-dione | 0.05% | 8 |
|  | 0.10% | 20 |
| Ethanol Control |  | 0 |

The second evaluation also involved 30 volunteers but included the cyclobutylidene homolog to broaden the comparison by including both adjacent homologs. Point totals indicating the degree of vasoconstriction elicited appear in Table II.

TABLE II

| Compound | Concentration | Total Points |
|---|---|---|
| 16α,17α-Cyclopentylidenedioxy-9α-fluoro-11β,21-dihydroxy-1,4-pregnadiene-3,20-dione 21-acetate | 0.05% | 43 |
|  | 0.10% | 48 |
| 16α,17α-Cyclobutylidenedioxy-9α-fluoro-11β,21-dihydroxy-1,4-pregnadiene-3,20-dione 21-acetate | 0.05% | 26 |
|  | 0.10% | 33 |
| 16α,17α-Cyclohexylidenedioxy-9α-fluoro 11β,21-dihydroxy-1,4-pregnadiene-3,20-dione 21-acetate | .05% | 33 |
|  | .10% | 34 |
| 9α-Fluoro-11β,21-dihydroxy-16α,17α-isopropylidenedioxy-1,4-pregnadiene-3,20-dione | .05% | 27 |
|  | .10% | 26 |

Results from both comparative evaluations clearly indicate the superior vasoconstriction properties of 16α,17α-cyclopentylidenedioxy-9α-fluoro-11β,21-dihydroxy-1,4-pregnadiene-3,20-dione 21-acetate. These results are particularly compelling in view of the consistent superior results achieved by the cyclopentylidene derivative when compared with the adjacent homologs.

The 16α,17α-cyclopentylidenedioxy-9α-fluoro-11β,21-dihydroxy-1,4-pregnadiene-3,20-dione 21-acetate may be incorporated into a variety of conventional pharmaceutical formulations providing topical preparations at concentrations of, for example, 0.01% to 0.5% in topical ointments, lotions or creams.

Compositions containing the active component of this invention may also be any of the standard pharmaceutical topical preparations such as solutions, suspensions, lotions, ointments, creams, unguents, sprays, powders, foams, etc. Excipients used in such preparations may include buffers such as phosphate, citrate or tartrate, surfactants such as polyoxyethylene (20) sorbitan monooleate (polysorbate 80) which is a complex mixture of polyoxyethylene ethers of mixed partial oleic esters of sorbitol anhydrides and oxylated tertiary octylphenol formaldehyde polymer, which is a surface tension reducing agent. Preservatives such as methyl and propyl parabens, which are the methyl and propyl esters of p-hydroxybenzoic acid, potassium sorbate, benzyl alcohol and the like can be used. Oils, waxes, fats, etc. are useful as emollients and ointment or emulsion bases such as petrolatum, wool fat (anhydrous lanolin), squalane, spermaceti and the like can also be useful. Stabilizers such as talc, clays, vegetable colloids, carboxymethylcellulose, carboxypolymethylene, and the like; and perfumes or fragrances such as lavender, lemon, gardenia, etc. may be found useful.

SPECIFIC DISCLOSURE

The following examples will serve to further illustrate the invention and show the preparation of the compound of the invention and formulations using the present compound.

EXAMPLE 1

Preparation of 16α,17α-Cyclopentylidenedioxy-9α-fluoro-11β,21-dihydroxy-1,4-pregnadiene-3,20-dione A 15 gm. (38.1 mmole) portion of 9α-fluoro-11β,16α,17α,21-tetrahydroxy-1,4-pregnadiene-3,20-dione is placed in a 500 ml. round bottom flask equipped with a magnetic stirrer bar and stopper. A 200 ml. (2.26 moles) portion of cyclopentanone and 30 drops of 70% aqueous perchloric acid are added and the suspension is stirred at room temperature for about 1½ hours. A pale yellow solution results. This solution is stored in a cold room for about 1 hour. A precipitate forms which is recovered by filtration, washed with n-hexane and air-dried yielding 3.6 gm. of product. The filtrate is concentrated under reduced pressure to about 25 ml. A solution of sodium bicarbonate is added until the concentrate is alkaline. A 25 ml. portion of chloroform is added and after mixing the concentrate is stored in a cold room overnight. A precipitate forms which is collected by filtration, washed with water until the washings are neutral to pH and air dried yielding an additional 8.4 gm. of product. The second filtrate is evaporated under reduced pressure to an oil. Acetone and activated charcoal are added, the mixture is filtered through diatomaceous earth and the filtrate is concentrated on a steam bath while adding n-hexane to the point of incipient crystallization. The mixture is allowed to stand overnight. The precipitate is collected by filtration, washed with acetone:n-hexane (1:9) and air dried yielding 2.7 gm. of product. The total yield for the subject product is 14.7 gm.

EXAMPLE 2

Preparation of 16α,17α-Cyclopentylidenedioxy-9α-fluoro-11β,21-dihydroxy-1,4-pregnadiene-3,20-dione 21-acetate An 11.1 gm. (24.1 mmole) portion of the product of Example 1 is placed in a 250 ml. round bottom flask. A 100 ml. portion of pyridine is added and the mixture is stirred to a complete solution. A 5.5 ml. (54.6 mmole) portion of acetic anhydride is added dropwise and the mixture is stirred for 2½ hours. An 11 ml. portion of methanol is added and the mixture is stirred an additional hour. This mixture is concentrated under reduced pressure to about 10–15 ml. and then poured slowly into a mixture of ice, water and dilute hydrochloric acid. This mixture is stirred and the solid which forms is collected by filtration, washed with water to a neutral pH and air dried yielding 11.5 gm. This solid is taken up in hot acetone, treated with activated charcoal and filtered while hot through diatomaceous earth. The filtrate is concentrated on a steam bath while adding n-hexane to the point of incipient crystallization. This mixture is allowed to cool to room temperature. The solid which forms is collected by filtration, washed with acetone:n-hexane (1:14) and air dried yielding 7.0 gm. of the desired product.

EXAMPLE 3

16α,17α-Cyclobutylidenedioxy-9α-fluoro-11β,21-dihydroxy-1,4-pregnadiene-3,20-dione 21-acetate A 39.5 g portion of 9α-fluoro-11β,16α,17α,21-tetrahydroxy-1,4-pregnadiene is placed in a one liter Erlenmeyer flask equipped with a magnetic stirring bar. A 500 ml portion of p-dioxane is added and the suspension is stirred at room temperature. A 14.0 g portion of cyclobutanone is added. A 10 ml portion of 70% aqueous perchloric acid is added dropwise with stirring. Sufficient p-dioxane is added to bring the total volume of p-dioxane to 600 ml and the reaction mixture is stirred at room temperature for 4½ hours. The reaction mixture is filtered. The filtrate is concentrated in vacuo on a warm water bath to about 285 ml and then poured into 3.5 liters of ice/water and stirred for 15 minutes. The mixture is stored in a cold room overnight and then the solid is recovered by filtration, washed with water and dried giving 24.5 g of 16α,17α-cyclobutylidenedioxy-9α-fluoro-11β,21-dihydroxy-1,4-pregnadiene-3,20-dione.

The above material is dissolved in 300 ml of pyridine in a 500 ml round bottomed flask equipped with a magnetic stirrer. A 10.4 ml portion of acetic anhydride is added slowly, with stirring. The mixture is stirred at room temperature overnight. A 25 ml portion of methanol is added to decompose the excess acetic anhydride and the mixture is allowed to stand for 30 minutes. The reaction mixture is concentrated to about 200 ml and then poured over about 4 liters of ice/water with stirring. The mixture is stored in a cold room overnight. The solid is recovered by filtration, washed with water until the washings are neutral and then dried giving crude 16α,17α-cyclobutylidenedioxy-9α-fluoro-11β,21-dihydroxy-1,4-pregnadiene-3,20-dione 21-acetate.

This product is purified as follows: The product is taken up in hot acetone which is then treated with activated charcoal and filtered through diatomaceous earth. The filtrate is concentrated on a steam bath while hexane is added. At the point of incipient crystallization, the heat is removed and the mixture is allowed to stand at room temperature overnight. The solid is recovered by filtration, washed with acetone:hexane (1:19) and then dried giving the desired purified 21-acetate product.

EXAMPLE 4

16α,17α-Cyclohexylidenedioxy-9α-fluoro-11β,21-dihydroxy-1,4-pregnadiene-3,20-dione 21-acetate A 25.0 g portion of 9α-fluoro-11β,16α,17α,21-tetrahydroxy-1,4-pregnadiene-3,20-dione is transferred to a 500 ml round bottomed flask equipped with a stirring bar. A 250 ml portion of cyclohexanone is added and the mixture is stirred. Fifty drops of 70% aqueous perchloric acid is added with continuous stirring. The reaction mixture is stirred for 45 minutes and then stored in a cold room for 3 hours. The solid is collected by filtration, washed with hexane and dried, giving 22.3 g of 16α,17α-cyclohexylidenedioxy-9α-fluoro-11β,21-dihydroxy-1,4-pregnadiene-3,20-dione.

A 25.0 g portion of the product, prepared as described above, is placed in a 500 ml round bottomed flask equipped with a magnetic stirrer. A 100 ml portion of pyridine is added and the mixture is stirred. A 13.3 ml portion of acetic anhydride is added with stirring to the reaction mixture with cooling in an ice/water bath. The cooling bath is removed and the mixture is allowed to stand with occasional stirring for 2 hours. A 20 ml portion of methanol is added with stirring to decompose the excess acetic anhydride and the mixture is stirred for 30 minutes. The reaction mixture is concentrated in vacuo to 30–50 ml and then poured onto about 1500 ml of an ice/water mixture with stirring. The solid is recovered by filtration, washed with water until the washings are neutral and dried giving crude 16α,17α-cyclohexylidenedioxy-9α-fluoro-11β,21 dihydroxy-1,4-pregnadiene-3,20-dione 21-acetate.

This product is purified as follows: The product is taken up in acetone, heated to boiling on a steam bath, treated with activated charcoal and filtered while hot through diatomaceous earth. The filtrate is concentrated on a steam bath while adding hexane to the point of incipient crystallization. The mixture is allowed to stand at room temperature for 3 hours. The solid is collected by filtration, washed with acetone:hexane (1:19) and dried giving the desired purified 21-acetate product.

EXAMPLE 5

Topical Cream Formulations Containing Variable Percentages of 16α,17α-Cyclopentylidenedioxy-9α-fluoro-11β,21-dihydroxy-1,4-pregnadiene-3,20-dione or the 21-Acetate thereof

| Ingredient | Percent Range (w/w) |
| --- | --- |
| Steroid | 0.01–0.5 |
| Glyceryl monostearate N.F. | 1–5 |
| Squalane* | 1–5 |
| Polysorbate 60** | 1–5 |
| Polysorbate 80 U.S.P.*** | 1–5 |
| Spermaceti | 5–20 |
| Stearyl alcohol U.S.P. | 5–20 |
| Sorbitol solution U.S.P. | 1–10 |
| Preservatives | 3–5 |
| Distilled water qs ad | 100 |

*Squalane = 2,6,10,15,19,23-Hexamethyltetracosane
**Polysorbate 60 = Polyoxyethylene sorbitan monostearate
***Polysorbate 80 = Polyoxyethylene sorbitan monooleate The ingredients are mixed in a conventional manner for preparing a pharmaceutical topical cream providing a white cream which may contain, for example, depending upon selected percentage of ingredients, such steroid percentages as 0.01, 0.025, 0.1 or 0.5%.

EXAMPLE 6

Topical Ointment Formulations Containing Variable Percentages of 16α,17α-Cyclopentylidenedioxy-9α-fluoro-11β,21-dihydroxy-1,4-pregnadiene-3,20-dione or the 21-Acetate thereof

| Ingredient | Percent Range (w/w) |
| --- | --- |
| Steroid | 0.01–0.5 |
| Polyethylene glycol 400 U.S.P. | 5–20 |
| White Petrolatum U.S.P. qs ad | 100 |

The ingredients are blended in a conventional manner providing a colorless topical ointment, which may provide, for example, such steroid percentages as 0.01, 0.025, 0.10 or 0.50%.

If desired, an antibacterial component such as neomycin may be added to the formulation in amounts ranging from 0.1% to 3% (w/w), as the sulfate in a micronized form.

EXAMPLE 7

Topical Foam Formulation Containing 16α,17α-Cyclopentylidenedioxy-9α-fluoro-11β,21-dihydroxy-1,4-pregnadiene-3,20-dione or the 21-Acetate thereof

| Ingredient | Weight Range/Container | |
| --- | --- | --- |
| Steroid | 0.5–50 | mg. |
| Arlacel ® 60* | 20–50 | mg. |
| Myrj 59 ®** | 300–500 | mg. |
| Glyceryl monostearate | 100–300 | mg. |
| Cetyl alcohol | 70–100 | mg. |
| Sorbitol 70% | 300–400 | mg. |
| Propylparaben | 3–5 | mg. |
| Methylparaben | 10–15 | mg. |
| Veegum Neutral ® | 15–20 | mg. |
| Distilled water | 6–10 | gm. |
| Freon 12/114 (40/60)*** | 1.3–2.0 | gm. |

*Arlacel ® = Sorbital monostearate
**Myrj ® = Polyoxyethylene derivative of fat forming fatty acids
***Freon ® = Dichlorodifluoromethane/1,2-dichloro-1,1,2,2-tetrafluoroethane The ingredients are blended in a conventional manner, filled in containers and then pressurized with Freon.

EXAMPLE 8

Ophthalmic Ointment Containing Variable Percentages of
16α,17α-Cyclopentylidenedioxy-9α-fluoro-11β,21-dihydroxy-1,4-pregnadiene-3,20-dione or the 21-Acetate thereof

| Ingredient | Percent Range (w/w) |
|---|---|
| Steroid | 0.01–0.5 |
| Mineral Oil, Light N.F. | 1–5 |
| White petrolatum qs ad | 100 |

The ingredients are blended in a conventional manner providing an off-white ophthalmic or otic preparation. Neomycin may be added as the micronized sulfate salt if an anti-bacterial ingredient is desired.

EXAMPLE 9

Topical Lotion Formulation Containing Variable Percentages of
16α,17α-Cyclopentylidenedioxy-9α-fluoro-11β,21-dihydroxy-1,4-pregnadiene-3,20-dione or the 21-Acetate thereof

| Ingredient | Percent Range (w/w) |
|---|---|
| Steroid | 0.01–0.5 |
| Polawax PD 34 ® * | 3–5 |
| Volpo 20 ® ** | 0.5–2 |
| Oleyl alcohol | 1–5 |
| Methylparaben | 0.12–0.2 |
| Propylparaben | 0.02–0.06 |
| Squalane | 1–5 |
| Potassium sorbate | 0.05–0.25 |
| Sorbitol 70% solution | 5–10 |
| Distilled water qs ad | 100 |

\* Polawax = Higher fatty alcohols and ethylene oxide reaction products
\*\* Volpo 20 = Polyoxyethylene ether of oleyl alcohol The ingredients are blended in a conventional manner to provide an opaque creamy lotion.

We claim:

1. A method of ameliorating inflammation in a mammal which comprises administering topically to said mammal an anti-inflammatory effective amount of 16α,17α-cyclopentylidenedioxy-9α-fluoro-11β,21-dihydroxy-1,4-pregnadiene-3,20-dione 21-acetate in association with a topical pharmaceutically acceptable carrier.

2. A method in accordance with claim 1, wherein the anti-inflammatory agent is incorporated in a topical cream.

3. A method in accordance with claim 1, wherein the anti-inflammatory agent is incorporated in a topical ointment.

4. A method in accordance with claim 1, wherein the anti-inflammatory agent is incorporated in a topical foam.

5. A method in accordance with claim 1, wherein the anti-inflammatory agent is incorporated in an ophthalmic ointment.

6. A method in accordance with claim 1, wherein the anti-inflammatory agent is incorporated in a topical lotion.

7. A method of treating inflammation in a mammal comprising administering topically to said mammal an anti-inflammatory effective amount of the steroid, 16α,17α-cyclopentylidenedioxy-9α-fluoro-11β,21-dihydroxy-1,4-pregnadiene-3,20-dione 21-acetate in association with a topical pharmaceutically acceptable carrier in which the steroid is present in a concentration range of from about 0.01% to about 0.50%.

* * * * *